United States Patent
Dwivedi et al.

(10) Patent No.: US 10,054,690 B2
(45) Date of Patent: Aug. 21, 2018

(54) LOW-COST DIGITAL PET DESIGN

(71) Applicant: KONINKLIJKE PHILIPS N.V., Eindhoven (NL)

(72) Inventors: Shekhar Dwivedi, Willoughby Hills, OH (US); Venudhar Rao Hajari, Mayfield Heights, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/538,210

(22) PCT Filed: Dec. 9, 2015

(86) PCT No.: PCT/IB2015/059461
§ 371 (c)(1),
(2) Date: Jun. 21, 2017

(87) PCT Pub. No.: WO2016/103090
PCT Pub. Date: Jun. 30, 2016

(65) Prior Publication Data
US 2018/0003828 A1    Jan. 4, 2018

Related U.S. Application Data

(60) Provisional application No. 62/095,805, filed on Dec. 23, 2014.

(51) Int. Cl.
  *G01T 1/161* (2006.01)
  *A61B 6/03* (2006.01)
  *A61B 6/00* (2006.01)
  *G01T 1/29* (2006.01)

(52) U.S. Cl.
  CPC .............. *G01T 1/161* (2013.01); *A61B 6/037* (2013.01); *A61B 6/5211* (2013.01); *G01T 1/2985* (2013.01)

(58) Field of Classification Search
  CPC ....... A61B 6/037; A61B 6/5211; G01T 1/161; G01T 1/2985
  See application file for complete search history.

(56) References Cited

U.S. PATENT DOCUMENTS

| 7,601,963 B2 | 10/2009 | Aykac |
| 8,729,480 B2 | 5/2014 | Vaquero |
| 8,866,086 B2 | 10/2014 | Michel |

(Continued)

FOREIGN PATENT DOCUMENTS

| JP | 2002197450 | 7/2002 |
| WO | 2013/126649 | 8/2013 |

OTHER PUBLICATIONS

Lerche, et al., "Maximum likelihood based positioning and energy correction for pixelated solid-state PET detectors", 2011 IEEE Nuclear Science Symposium and Medical Imaging Conference.

*Primary Examiner* — Marcus Taningco

(57) ABSTRACT

A diagnostic imaging system utilizing a reduced crystal design pattern is utilized to image a subject and collect event data. The reduced crystal design pattern includes filled crystal locations and empty crystal locations. A processor accounts for empty crystal locations by selecting windows that include nearest neighbor filled crystal locations. The nearest neighbor filled crystal locations include event data which is averaged by the processor and assigned to the empty crystal location. A weighted average based on distance or event strength is incorporated.

19 Claims, 3 Drawing Sheets

(56) References Cited

U.S. PATENT DOCUMENTS

| | | | |
|---|---|---|---|
| 2003/0095631 A1* | 5/2003 | Rosner | G01N 23/02 378/98.12 |
| 2005/0063513 A1* | 3/2005 | Hsieh | A61B 6/032 378/98.8 |
| 2005/0111610 A1 | 5/2005 | De Man | |
| 2006/0262147 A1* | 11/2006 | Kimpe | G09G 3/20 345/690 |
| 2007/0205367 A1 | 9/2007 | Deman | |
| 2009/0032717 A1* | 2/2009 | Aykac | G01T 1/2018 250/367 |
| 2011/0127436 A1* | 6/2011 | Hashizume | G01T 1/1611 250/363.04 |
| 2013/0016805 A1 | 1/2013 | Silver | |
| 2013/0032721 A1* | 2/2013 | Michel | G01T 1/202 250/362 |
| 2013/0126742 A1 | 5/2013 | Hayun | |
| 2013/0320222 A1* | 12/2013 | Abenaim | A61B 6/032 250/366 |
| 2014/0264041 A1* | 9/2014 | Schulz | G01T 1/2985 250/362 |
| 2016/0183893 A1* | 6/2016 | Zhang | A61B 6/0407 250/363.05 |

\* cited by examiner

LOW-COST DIGITAL PET DESIGN

CROSS REFERENCE TO RELATED APPLICATIONS

This application is the U.S. National Phase application under 35 U.S.C. § 371 of International Application No. PCT/IB2015/059461 filed Dec. 9, 2015, published as WO 2016/103090 on Jun. 30, 2016, which claims the benefit of U.S. Provisional Patent Application No. 62/095,805 filed Dec. 23, 2014. These applications are hereby incorporated by reference herein.

BACKGROUND

The following relates generally to radioemission imaging. It finds particular application in conjunction with positron emission tomography (PET), and will be described with particular reference thereto. A digital PET scanner has several benefits in terms of image quality, but it is costly to design a digital PET scanner. For example, in one design there are over 30,000 crystals to build the illustrative PET scanner.

The crystal cost is a substantial portion of the overall PET system cost, and reducing the crystal cost would make PET scanners more affordable for less affluent medical facilities, such as those in developing countries. However, since each crystal corresponds to a detector pixel, reducing the number of crystals results in a corresponding reduction in PET detector resolution and hence a corresponding reduction in image resolution.

SUMMARY

The following provides a new and improved system and method which overcome these problems and others.

In accordance with one aspect, a nuclear imaging system comprises a radiation detector having a regular array of detector pixel locations and including: radiation detector elements occupying some of the detector pixel locations of the regular array, and unoccupied detector pixel locations of the regular array that are not occupied by radiation detector elements. The system may further include one or more processors configured to process radiation event data acquired of a subject using the radiation detector to generate a reconstructed image of the subject by operations including: estimating radiation event data for the unoccupied detector pixel locations based on radiation event data acquired of the subject by radiation detector elements occupying detector pixel locations of the regular array that neighbor the unoccupied detector pixel locations; and reconstructing a data set including both the radiation event data acquired of the subject using the radiation detector and the estimated radiation event data for the unoccupied detector pixel locations to generate the reconstructed image of the subject.

In accordance with another aspect, an imaging method comprises: acquiring radiation event data of a subject in an imaging region using at least one crystal module arranged around the imaging region, the module having scintillator crystals defining a regular array of detector pixels with some missing detector pixels; estimating radiation event data for the missing detector pixels; and reconstructing the combination of the acquired radiation event data and the estimated radiation event data to generate a reconstructed image of the subject.

In accordance with another aspect, an imaging system comprises: a radioemission imaging scanner including a scintillator-based radiation detector with some missing scintillator crystals; and a processor programmed to reconstruct acquired radioemission data acquired by the radioemission imaging scanner by operations including: estimating radioemission data for the missing scintillator crystals based on the acquired radioemission data, and reconstructing the combination of the acquired radioemission data and the estimated radioemission data for the missing scintillator crystals to generate a reconstructed image.

One advantage resides in reduced cost of an imaging system.

Another advantage resides in little loss in image quality.

Still further advantages of the present invention will be appreciated to those of ordinary skill in the art upon reading and understand the following detailed description.

BRIEF DESCRIPTION OF DRAWINGS

The present application may take form in various components and arrangements of components, and in various steps and arrangements of steps. The drawings are only for purposes of illustrating the preferred embodiments and are not to be construed as limiting the invention.

DETAILED DESCRIPTION

Disclosed herein is a PET scanner with a reduced number of scintillator crystals to reduce production costs of scanners without a corresponding loss of image fidelity.

Figure 1:
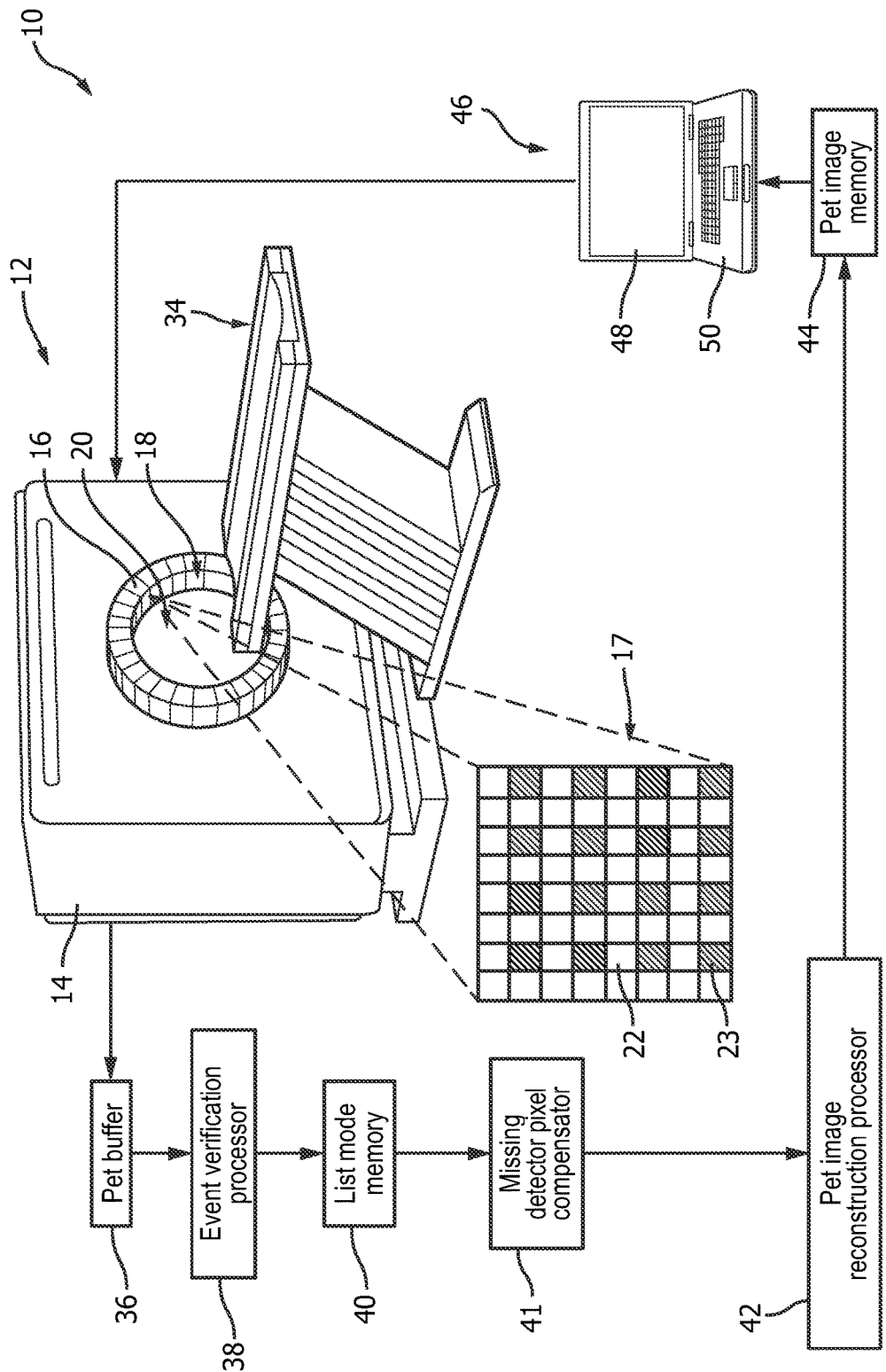
FIG. 1 illustrates a nuclear imaging system with an iterative-based reconstruction system using an in-reconstruction filter for smoothing.

With reference to FIG. 1, a nuclear imaging system 10 employing a nuclear imaging modality to image a subject is provided. The nuclear imaging modality detects radiation, such as gamma photons, received from a target volume of the subject for imaging. Examples of such nuclear (also called radioemission) imaging modalities include positron emission tomography (PET) and single-photon emission computed tomography (SPECT). As illustrated, the system 10 is a PET imaging system.

The system 10 includes a nuclear scanner 12, illustrated as a PET scanner. The nuclear scanner 12 generates raw scan data and includes a stationary gantry 14 housing a plurality of gamma detectors 16 built up from individual detector array units 17 (variously referred to in the art as "modules", "tiles", or so forth) arranged around a bore 18 of the scanner 12. FIG. 1 shows a plan view of one such detector module 17 as a representative inset. The bore 18 defines an examination volume 20 for receiving a target volume of a subject to be imaged, such as a brain, torso, or the like. The detectors 16 are typically arranged in one or more stationary rings which extend the length of the examination volume 20. However, rotatable heads are also contemplated. The detectors 16 detect gamma photons from the examination volume 20 and generate the raw scan data.

Figure 2:
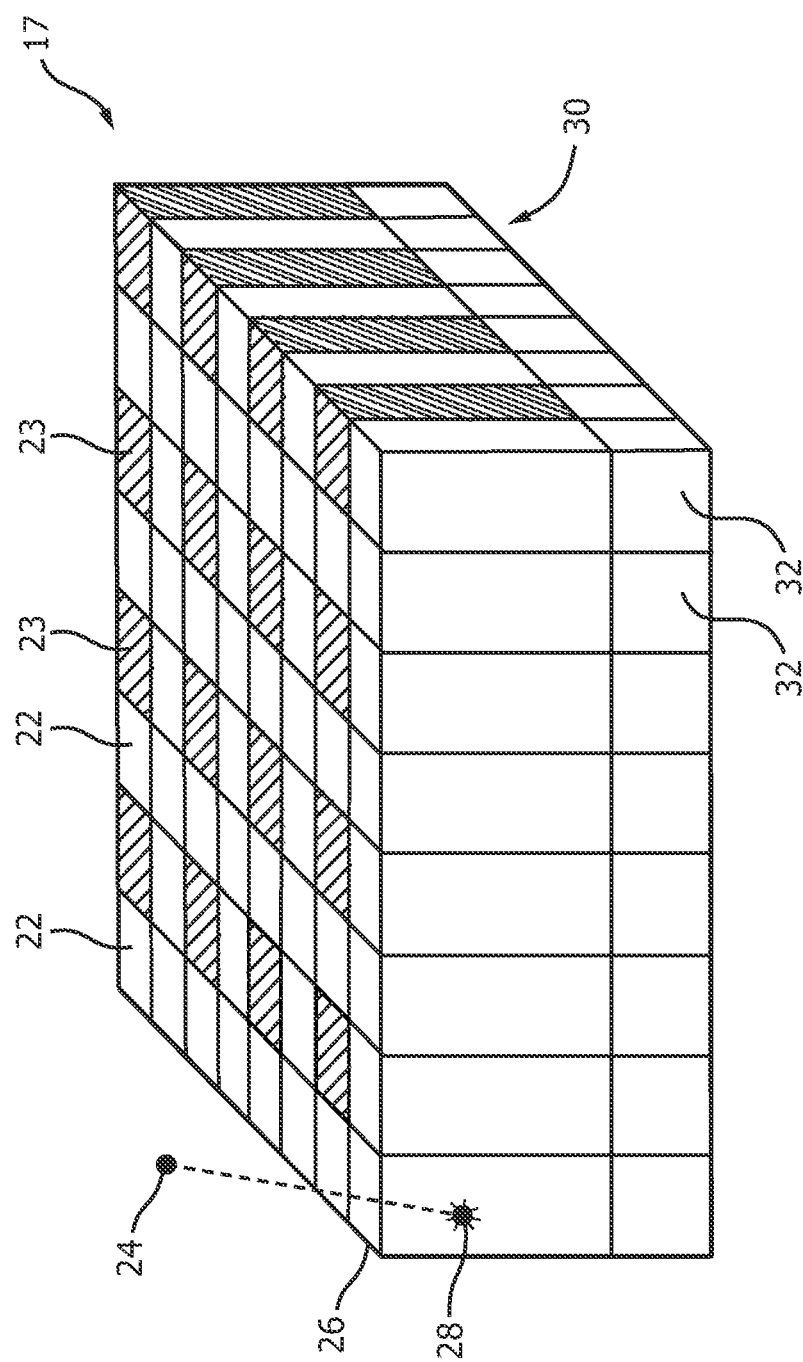
FIG. 2 illustrates a typical detector of the nuclear imaging system of FIG. 2.

With reference to FIG. 2, each of the detector modules 17 includes one or more scintillators 22 typically arranged in a regular grid pattern. The pattern of scintillators 22 is further described in detail below. The scintillators 22 scintillate and generate visible light pulses in response to energy depositions by gamma photons. As illustrated, a gamma photon 24 deposits energy in a scintillator 26, thereby resulting in a visible light pulse 28. The magnitude of a visible light pulse is proportional to the magnitude of the corresponding energy deposition. Examples of scintillators 22 include sodium iodide doped with thallium (NaI(Tl)), cerium-doped lutetium yttrium orthosilicate (LYSO) and cerium doped lutetium oxyorthosilicate (LSO).

In addition to the scintillators 22, the detector module 17 includes a sensor 30 detecting the visible light pulses in the scintillators 22. The sensor 30 includes a plurality of light sensitive elements 32. The light sensitive elements 32 are arranged in a grid of like size as the grid of scintillators 22 and optically coupled to corresponding scintillators 22. In the illustrated embodiment, the light sensitive elements 32 are silicon photomultipliers (SiPMs), but photomultiplier tubes (PMTs) are also contemplated as well as digital silicon photomultipliers (dSiPMs). In illustrative FIG. 2 there is a one-to-one correspondence between the scintillator crystals 22 and the SiPMs 32, but this is not required—for example, in another embodiment there is a four-to-one scintillator-to-SiPM ratio in which each SiPM is covered by a 2×2 array of scintillator crystals.

Each of the SiPMs 32 includes a photodiode array (e.g., Geiger-mode avalanche photodiode arrays), each photodiode corresponding to a cell of the photodiode array. Suitably, the SiPMs 32 are configured to operate in a Geiger mode to produce a series of unit pulses to operate in a digital mode. Alternatively, the SiPMs can be configured to operate in an analog mode. Where the light sensitive elements 32 are PMTs, there is often a many-to-one correspondence between the scintillators 22. Regardless of the scintillator-to-detector element ratio, in a typical configuration each scintillator crystal serves as a detector "pixel", that is, the detected scintillation 28 is localized to a single identified scintillator crystal 22. To this end, the scintillator crystal 22 may be coated with a light-reflective material to contain the scintillation light in the crystal. Additionally or alternatively, signal processing techniques such as Anger logic may be employed to locate which scintillator crystal detected the scintillation event 28. It is also contemplated to further localize the scintillation event within the scintillator crystal 22 in which it occurs—for example, a depth of interaction (DOI) analysis may be performed based on the spread of light observed at the light detector 30.

The scintillator crystals 22 are arranged in a regular (e.g. Cartesian) grid, for example rows and columns of scintillator crystals 22. More generally, a regular array or regular grid of detector pixel locations comprises detector pixel locations arranged in a repeating pattern across the face of the detector, e.g. in Cartesian rows and columns in the illustrative examples, or in a regular hexagonal layout with a hexagonal repeating primitive unit repeated over the detector face, or so forth).

However, as seen in FIG. 2 some scintillator crystals are omitted from the regular grid. In illustrative FIG. 2 these "missing" scintillator crystals are replaced by filler elements 23, for example glass elements cut to the same shape as the scintillator crystals 22. Substituting filler elements 23 for missing scintillator crystals can have advantages in terms of improved structural integrity of the scintillator array, since in some designs neighboring crystals may be in contact and such contact contributes to structural strength of the overall layout. However, it is also contemplated to omit the filler elements 23 and instead have unfilled openings in the (otherwise) regular grid of scintillator crystals 22. The filler elements 23, if used, should be inexpensive (at least compared with the scintillator crystals 22)—for example, the cost of a single LYSO crystal is on the order of $10 USD, whereas an equivalently sized glass element purchased in bulk is much less expensive than this. Thus, the omitted scintillator crystals represent a substantial cost savings. The filler elements 23 are made of a material (e.g. glass) that does not produce an appreciable scintillation in response to absorption of a gamma ray, or the filler elements 22 do not absorb gamma rays at all (i.e. are transparent to the gamma rays).

More generally, the radiation detector has a regular array of detector pixel locations and includes: (i) radiation detector elements 22 (e.g. scintillator crystals 22) occupying some of the detector pixel locations of the regular array, and (ii) unoccupied detector pixel locations of the regular array that are not occupied by radiation detector elements. In the scintillator-based embodiment of FIG. 2, the scintillator crystal 22 is the radiation detector element, since the scintillator crystal 22 absorbs the radiation particle 24 thus effectuating its detection. In illustrative embodiments, the unoccupied detector pixel locations (that is, the missing detector pixels) are arranged in a regular sub-array, e.g. as shown in the illustrative examples of FIG. 3.

The illustrative detector module 17 includes an 8×8 array of scintillator crystals 22, but other sizes are contemplated. Moreover, various module/submodule combinations are contemplated depending upon the sizes of constituent elements, with various nomenclatures for the various modules and sub-modules, e.g. "tiles", "podules", "modules", or so forth. It is appreciated that that the shown geometries are merely illustrative examples, and other geometries with other fill factors can be used and are contemplated.

Referring back to FIG. 1, during a scan of a subject using the scanner 12, a target volume of the subject is injected with a radiopharmaceutical or radionuclide. The radiopharmaceutical or radionuclide emits gamma photons, or causes gamma photons to be emitted, from the target volume. The target volume is then positioned in the examination volume 20 using a subject support 34 corresponding to the scanner 12. Once the target volume is positioned within the examination volume 20, the scanner 12 is controlled to perform a scan of the target volume and event data is acquired. The acquired event data describes the time, location and energy of each scintillation event detected by the detectors 16 and is suitably stored in a data buffer 36, illustrated as a PET data buffer.

Subsequent to acquisition, or concurrently therewith, an event verification processor 38 filters the buffered event data. The filtering includes comparing energy (cell counts in the digital mode) of each scintillation event to an energy window, which defines the acceptable energy range for scintillation events. Those scintillation events falling outside the energy window are filtered out. Typically, the energy window is centered on the known energy of the gamma photons to be received from the examination volume 20 (e.g., 511 kiloelectron volt (keV)) and determined using the full width half max (FWHM) of an energy spectrum generated from a calibration phantom.

For PET imaging, the event verification processor 38 further generates lines of response (LORs) from the filtered event data. A LOR is defined by a pair of gamma photons striking the detectors 16 within a specified time difference of each other (i.e., a coincident event). The specified time difference is small enough to ensure the gammas are from the same annihilation event. For SPECT imaging, the event verification processor 38 further generates a projection line or small-angle cone (generally referred to as a "projection"). A projection is defined by a gamma photon striking the detectors 16. The LORs or the projections are stored in a list of a list mode memory 40. Each list item corresponds to a LOR or a projection.

When using detectors 16 comprising detector modules 17 with missing scintillator crystals (e.g. replaced by the filler elements 23), no gamma rays are detected by these missing scintillator crystals. If the number of missing scintillator crystals were sufficiently small, then this would not be a significant problem as the effect would be statistically insignificant. However, in the embodiments disclosed herein, the missing crystals amount to a substantial fraction of the total number of scintillator crystals that would be present in a completely filled regular array. For example, the module 17 would, if completely filled, have 8×8=64 scintillator crystals 22. As seen FIG. 2 (or in the inset of FIG. 1), there are 16 missing scintillator crystals in the detector module 17—that is, 25% of the crystals of the "filled" 8×8 array are missing. In other embodiments disclosed herein (see FIG. 3) the fraction of crystals missing may be 50% or even 75% (other fractions of missing crystals are also contemplated). Accordingly, the "lost" gamma ray acquisitions due to this large fraction of missing scintillator crystals is substantial.

With continuing reference to FIG. 1, to compensate for these lost acquisitions, a missing detector pixel compensator 41 generates estimated, i.e. approximate, data for each missing scintillator crystal based on the acquisition statistics of the neighboring scintillator crystals 22 that are present, as disclosed herein. The approximate data are suitably formatted in list mode format with the event detector location corresponding to the missing scintillator crystal. Thus, the output of the missing detector pixel compensator 41 is a "full" list mode data set can thereafter be processed as if it had been acquired by detectors 16 having no missing detector pixels.

A reconstruction processor 42, illustrated as a PET reconstruction processor, reconstructs the list mode data (i.e., a list of projections or LORs, depending upon the imaging modality, with the estimated data for missing scintillator crystals filled in by the missing detector pixel compensator 41) into a reconstructed image of the target volume that is stored, e.g. in a PET image memory 44, and/or is displayed on a display device 48 or so forth. The various data processing components 38, 41, 42 are suitably implemented as a computer 46 or other electronic data processing device programmed by suitable software or firmware to perform the various functionality as disclosed herein. The computer 46 or other electronic data processing device may be further programmed to serve as a controller or user interface via which a radiology technician or other medical personnel operate the imaging scanner 12 using suitable user interface device (s) such as an illustrative keyboard 50, mouse, trackball, touch-sensitive display, or so forth. It will also be appreciated that the various data processing components 38, 41, 42 can be implemented as separate components (as shown) or can be variously integrated together—for example, the missing detector pixel compensator function can be integrated with the event verification component to generate the list mode data.

Figure 3:
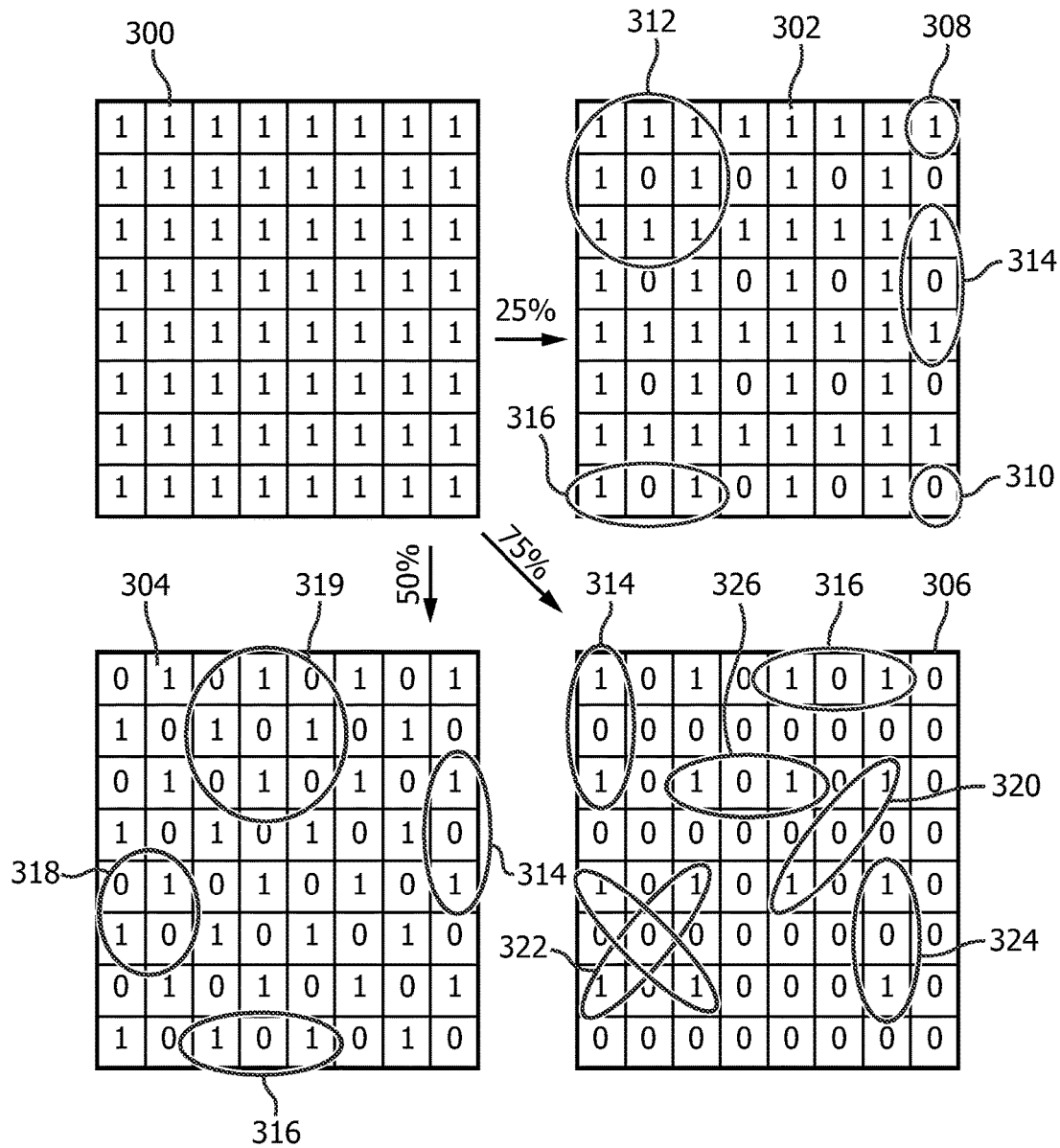
FIG. 3 illustrates reduced crystal designs.

With reference to FIG. 3, some illustrative reduced crystal design patterns for the detector module are depicted. The full pattern 300 is the conventional crystal design pattern for a crystal module where every crystal location is occupied by a scintillator crystal 22, i.e. 100% crystal capacity. In one embodiment, a reduced pattern that eliminates 25% 302 of the crystals is used. (This corresponds to the illustrative detector module 17 of FIG. 1, inset and FIG. 2.) In another embodiment, a reduced pattern that eliminates 50% 304 of the crystals is used. In another embodiment, a reduced pattern that eliminates 75% 306 of the crystals is used. The patterns will be discussed in further detail below. It is appreciated that the patterns shown in FIG. 3 are diagrammatic tabular representations with numerical indicators depicting the absence/presence of crystals, where each square, i.e. table entry, represents a potential crystal location. In this case, "1" indicates the presence of a crystal 308 at a crystal location and "0" indicates the absence of a crystal 310 at a crystal location. In some embodiments, the missing detector pixels are themselves arranged in a regular grid or array, as this can simplify computing estimated data for the missing detector pixels, as described herein.

As stated above, list mode data is acquired of a subject using a reduced crystal pattern. Due to the reduced crystal pattern design, the missing detector pixel compensator 41 accounts for missing event data at the pixels where crystals are absent 310 by adding estimated data for those missing pixels based on the actual acquisition statistics of neighboring detector pixels (including directly neighboring, i.e. adjacent, detector pixels and optionally also including further-distant, e.g. next-nearest neighboring, detector pixels).

In one embodiment, the missing detector pixel compensator 41 accounts for the missing crystals by using an average of event data, i.e. singles counts, from adjacent crystals. For example, in the 25% reduced crystal design pattern 302 (upper right example of FIG. 3, also corresponds to the illustrative detector module 17 of FIG. 1, inset, and FIG. 2), a 3×3 window 312 can be selected to include 8 filled crystal locations surrounding an absent crystal location. The missing detector pixel compensator 41 averages the event data of the 8 nearest neighbor crystal locations and stores the average as the event data corresponding to the absent crystal location. For absent crystal locations on the edge of the module, and 3×1 window 314 or a 1×3 window 316 can be used to average event data of the filled crystal locations and store the average as the event data for the absent crystal location. It is contemplated that other sized windows can be used.

In another example, in the 50% reduced crystal design pattern 304, a 2×2 window 318 3×3 window 319 can be used to average event data of the filled nearest neighbor crystal locations and store the average as the event data for the absent crystal location. For absent crystal locations on the edge of the module, and 3×1 window 314 or a 1×3 window 316 can be used to average event data of the filled crystal locations and store the average as the event data for the absent crystal location. It is contemplated that other sized windows can be used.

In yet another example, in the 75% reduced crystal design pattern 306, a pair of nearest neighbor diagonal adjacent filled crystals 320 or two pairs of nearest neighbor diagonal adjacent filled crystals 322 can be used to average event data of the filled crystal locations and store the average as the event data for the absent crystal location. For absent crystal locations 310 that do not have diagonal adjacent filled crystals, a 3×1 window 324 or 1×3 window 326 can be used to average event data of the filled crystal locations and store the average as the event data for the absent crystal location. For absent crystal locations on the edge of the module, and 3×1 window 314 or a 1×3 window 316 can be used to average event data of the filled crystal locations and store the average as the event data for the absent crystal location. It is contemplated that other sized windows can be used.

In these examples, only immediately neighboring, i.e. adjacent, detector elements are used in estimating the data for the missing scintillator crystal. In another approach, further-distant crystals may also be factored in. For example, next-nearest neighbor elements may be added in. In such a case, since the next-nearest neighbor crystal data are not likely to be as representative as the nearest neighbor pixels, the data can be weighted accordingly, i.e. a lower weight assigned to data from next-nearest neighbor crystals as compared with nearest neighbor crystals.

To implement the missing detector pixel compensator 41, a table can be provided, with an entry for each missing detector element (i.e. each missing scintillator crystal) that identifies the extant detector elements that are to be combined to estimate data for the missing detector element along with the weight to assign to the data from each extant scintillator crystal. The estimation can then be rapidly performed as it merely requires retrieving the extant crystal data, weighting, and summing.

More particularly, in one embodiment, the missing detector pixel compensator 41 adopts a weighted average approach to construct event data values for absent crystal locations 310. The event verification processor 38 uses a linear or non-linear weight guided function designed to determine the events at the absent crystal location. The weights of the function can be chosen using various weighting schemes. In one embodiment, the weights are chosen using a distance guided approach. The distance guided approach considers the distance of absent crystal locations 310 to filled crystal locations 308 as a factor to determine the weight to be given to the events at a particular crystal (i.e., data from directly adjacent crystals is weighted more heavily than next-nearest neighbor crystals, et cetera). In another embodiment, the event verification processor 38 considers the strength, i.e. number of singles counts, of events at a filled crystal location 308 to determine weighting for that location.

The foregoing can be directly applied in the case of single photon emission computed tomography (SPECT) data, because in SPECT each detector pixel acquires lines-of-response (LORs) independently of the other detector pixels. By contrast, in PET each LOR is defined by two (nearly) simultaneous 511 keV gamma particle detection events. To account for this, the described averaging can be performed for each detector pixel pair. For example, consider the LOR (i,j) defined between detector pixels indexed i and j, where detector pixel i is a missing pixel and detector pixel j is an existing detector pixel. The LOR count between each existing detector pixel neighboring the missing pixel i and detector pixel j can then be averaged. In the case of estimating a LOR (i,j) where both detector elements i and j are missing, various approaches can be taken. In one approach, these data are omitted from the list mode data set that is reconstructed. Although this may impact the reconstructed image quality to some extent, the impact is relatively low, especially for designs in which the fraction of detector pixels missing is low, e.g. 25% as in the embodiment of FIG. 1, inset, and FIG. 2. Another approach is to: (1) estimate for LOR (i,j+1) where "j+1" denotes an existing immediately neighboring pixel to missing detector j (so that the situation is converted to the just-described one-missing-pixel case); (2) estimate for LOR (i+1,j) where "i+1" denotes an existing immediately neighboring pixel to missing detector i; and (3) averaging the results of steps (1) and (2). Optionally, this may be repeated for some or all of the surrounding pixels of the missing pixels i and j, depending upon the desired balance between computational complexity and estimation quality.

Depending upon the nature of the image reconstruction performed by the reconstruction processor 42, the estimated LORs for missing detector pixels may need to be assigned estimated time stamps. (The time stamp values are not of significance if, for example, the image reconstruction performs forward/backward projection all LORs of the data set without regard to time information). For a static imaging subject which does not move or otherwise change over time, the time stamps for missing detector pixels can be assigned random or pseudorandom values within the time interval of the data acquisition, so as to uniformly fill the time interval. If it is desired to estimate variation in time of the time stamp statistics (as might be appropriate if, for example, in a dynamic imaging task in which inflow/washout of the radiopharmaceutical is measured) then the time stamp distributions over the acquisition time interval for the neighboring detector pixels can be chosen as a "template" and the time stamps for the estimated LORs of the missing detector pixel chosen to conform with that statistical distribution.

In one embodiment, reduced scan times are achieved due to the reduced number of crystals in the standard field of view. In another embodiment, reduced scan times are achieved by increasing the spacing between full detector blocks and increasing the field of view.

Referring back to FIG. 1, a control system, such as the illustrative computer 46, suitably provides a graphical user interface (GUI) to allow users to control the scanner 12 to image a subject. For example, the user can coordinate a PET image of a target volume of the subject. Further, by way of the GUI, the control system can be employed to view and, optionally, manipulate images stored in the image memory 44. For example, an image of the image memory can be displayed on the display device 48.

In some instances, one or more of the memories 36, 40, 44 and/or the processing components 38, 41, 4 are integrated with the control system, e.g. as a unitary computer system 46. For example, the reconstruction processor 42, the missing detector pixel compensator 41, and the event verification processor 38 can share a common processor.

As used herein, a memory includes any device or system storing data, such as a random access memory (RAM) or a read-only memory (ROM), a hard disk drive, optical disk, or so forth. Further, as used herein, a processor includes any device or system processing input device to produce output data, such as a microprocessor, a microcontroller (typically with ancillary components such as working RAM memory), a graphic processing unit (GPU), an application-specific integrated circuit (ASIC), an field-programmable gate array (FPGA), and the like; a controller includes any device or system controlling another device or system, and typically includes at least one processor; a user input device includes any device, such as a mouse or keyboard, allowing a user of the user input device to provide input to another device or system; and a display device includes any device for displaying data, such as a liquid crystal display (LCD) or a light emitting diode (LED) display.

The illustrative embodiments employ a radiation detector design in which each detector pixel corresponds to a single scintillator crystal 22. Functionally, a detector pixel is the smallest element of the radiation detector to which a radiation detection event can be localized (although some further ancillary localization, such as DOI, may be possible). The detector pixel size thus determines the spatial resolution of the radiation detector. In another contemplated embodiment, direct-detection solid state detector elements are employed, in which radiation is directly detected by absorption of a radiation particle by a solid state detector without an intervening scintillator/scintillation event generating light. In a solid state detector, the detector pixel corresponds to a single solid state detector element that generates a current pulse (or other signal) in response to absorbing a radiation particle. Analogously to scintillator-based embodiments disclosed herein, such a solid state detector can be advantageously constructed in accord with the principles disclosed herein by omitting certain solid state detector elements from the regular array of solid state detector elements making up the radiation detector, and estimating LORs for the missing solid state detector elements based on LOR data acquired by neighboring solid state detector elements.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A positron emission tomography (PET) imaging system comprising:
    a radiation detector having a regular array of detector pixel locations and including:
        radiation detector elements occupying some of the detector pixel locations of the regular array, and
        unoccupied detector pixel locations of the regular array that are not occupied by radiation detector elements; and
    one or more processors configured to process radiation event data acquired of a subject using the radiation detector to generate a reconstructed image of the subject by operations including:
        estimating radiation event data for the unoccupied detector pixel locations based on radiation event data acquired of the subject by radiation detector elements occupying detector pixel locations of the regular array that neighbor the unoccupied detector pixel locations wherein for each unoccupied detector pixel location i radiation event data is estimated for each line of response (LOR) (i,j) defined between the unoccupied detector pixel location i and a detector pixel location j; and
        reconstructing a data set including both the radiation event data acquired of the subject using the radiation detector and the estimated radiation event data for the unoccupied detector pixel locations to generate the reconstructed image of the subject.

2. The PET imaging system according to claim 1 wherein the estimating comprises:
    for each LOR (i,j), estimating radiation event data for the unoccupied detector pixel location i based on radiation event data acquired of the subject by radiation detector elements occupying detector pixel locations within a window defined around the unoccupied detector pixel location i.

3. The PET imaging system according to claim 2 wherein the estimating includes:
    weighting event data acquired by radiation detector elements occupying detector pixel locations within the window defined around the unoccupied detector pixel location i according to a distance from the unoccupied detector pixel location i.

4. The PET imaging system according to claim 2, wherein the regular array of detector pixel locations is a Cartesian array with rows and columns of detector pixel locations, and the window defined around the unoccupied detector pixel location is one of a 3×3, 3×1, 1×3, 2×2 crystal locations or diagonal adjacent crystal locations.

5. The PET imaging system according to claim 1, wherein the regular array of detector pixel locations is a Cartesian array with rows and columns of detector pixel locations and the unoccupied detector pixel locations are 25%, 50%, or 75% of the detector pixel locations of the radiation detector.

6. The PET imaging system according to claim 5, wherein the regular array of detector pixel locations is a Cartesian array with rows and columns of detector pixel locations including occupied and unoccupied detector pixel locations according to one of:

| 1 | 1 | 1 | 1 | 1 | 1 | 1 | 1 |
|---|---|---|---|---|---|---|---|
| 1 | 0 | 1 | 0 | 1 | 0 | 1 | 0 |
| 1 | 1 | 1 | 1 | 1 | 1 | 1 | 1 |
| 1 | 0 | 1 | 0 | 1 | 0 | 1 | 0 |
| 1 | 1 | 1 | 1 | 1 | 1 | 1 | 1 |
| 1 | 0 | 1 | 0 | 1 | 0 | 1 | 0 |
| 1 | 1 | 1 | 1 | 1 | 1 | 1 | 1 |
| 1 | 0 | 1 | 0 | 1 | 0 | 1 | 0 |

Or

| 0 | 1 | 0 | 1 | 0 | 1 | 0 | 1 |
|---|---|---|---|---|---|---|---|
| 1 | 0 | 1 | 0 | 1 | 0 | 1 | 0 |
| 0 | 1 | 0 | 1 | 0 | 1 | 0 | 1 |
| 1 | 0 | 1 | 0 | 1 | 0 | 1 | 0 |
| 0 | 1 | 0 | 1 | 0 | 1 | 0 | 1 |
| 1 | 0 | 1 | 0 | 1 | 0 | 1 | 0 |
| 0 | 1 | 0 | 1 | 0 | 1 | 0 | 1 |
| 1 | 0 | 1 | 0 | 1 | 0 | 1 | 0 | or

| 1 | 0 | 1 | 0 | 1 | 0 | 1 | 0 |
|---|---|---|---|---|---|---|---|
| 0 | 0 | 0 | 0 | 0 | 0 | 0 | 0 |
| 1 | 0 | 1 | 0 | 1 | 0 | 1 | 0 |
| 0 | 0 | 0 | 0 | 0 | 0 | 0 | 0 |
| 1 | 0 | 1 | 0 | 1 | 0 | 1 | 0 |
| 0 | 0 | 0 | 0 | 0 | 0 | 0 | 0 |
| 1 | 0 | 1 | 0 | 1 | 0 | 1 | 0 |
| 0 | 0 | 0 | 0 | 0 | 0 | 0 | 0 | where each table cell corresponds to a detector pixel location, a "1" in a table cell indicates a filled detector pixel location, and a "0" in a table cell indicates an unfilled detector pixel location.

7. The PET imaging system according to claim 1, wherein each radiation detector element comprises a scintillator crystal and the unoccupied detector pixel locations of the regular array are not occupied by scintillator crystals.

8. The PET imaging system according to claim 1, wherein the nuclear imaging system includes a scanner with an increased field of view and increased spacing between radiation detector elements.

9. The PET imaging system according to claim 1 wherein the unoccupied director pixel locations are a predefined shape and size.

10. A positron emission tomography (PET) imaging method comprising:
    acquiring radiation event data of a subject in an imaging region using at least one crystal module arranged around the imaging region, the module having scintillator crystals defining a regular array of detector pixels with some missing detector pixels, the radiation event data comprising line of response (LOR) data;
    estimating radiation event data for each missing detector pixel i by estimating each LOR (i,j) defined between the missing detector pixel i and a detector pixel j; and
    reconstructing the combination of the acquired radiation event data and the estimated radiation event data to generate a reconstructed image of the subject.

11. The PET imaging method according to claim 10, wherein the estimating comprises:

estimating radiation event data for each missing detector pixel i based on radiation event data acquired by detector pixels in a window that includes the missing detector pixel i.

12. The PET imaging method according to claim 11, further comprising:
   for each LOR (i,j), averaging the LORs acquired by the detector pixels in the window and the detector pixel j; and
   assigning the average event data to the LOR (i,j) defined between the missing detector pixel i and the detector pixel j.

13. The PET imaging method according to claim 12, further comprising:
   weighting the radiation event data acquired by the detector pixels in the window according to distance from the missing detector pixel i.

14. The PET imaging method according to claim 11, wherein the window is one of a 3×3, 3×1, 1×3, 2×2 crystal locations or diagonal adjacent crystal location.

15. The PET imaging method according to claim 10, wherein a regular array of detector pixels has between 25% and 75% missing detector pixels.

16. An imaging system, comprising:
   a radioemission imaging scanner including a scintillator-based radiation detector including scintillator crystals arranged in a grid with some missing scintillator crystals and light sensitive elements arranged in a grid and optically coupled with the scintillator crystals wherein the light sensitive elements include light sensitive elements corresponding to the missing scintillator crystals; and
   a processor programmed to reconstruct acquired radioemission data acquired by the radioemission imaging scanner by operations including:
      estimating radioemission data for the missing scintillator crystals based on the acquired radioemission data, and
      reconstructing the combination of the acquired radioemission data and the estimated radioemission data for the missing scintillator crystals to generate a reconstructed image.

17. The imaging system of claim 16 wherein the radioemission imaging scanner is a positron emission tomography scanner.

18. The imaging system of claim 16 wherein the radiation detector includes filler elements substituted for the missing scintillator crystals.

19. The imaging system of claim 16 wherein there is a one-to-one correspondence between the scintillator crystals and the light sensitive elements.

* * * * *